Nov. 10, 1970 W. A. WARRINER Plant Pat. 2,997
ROSE PLANT
Filed Dec. 9, 1968
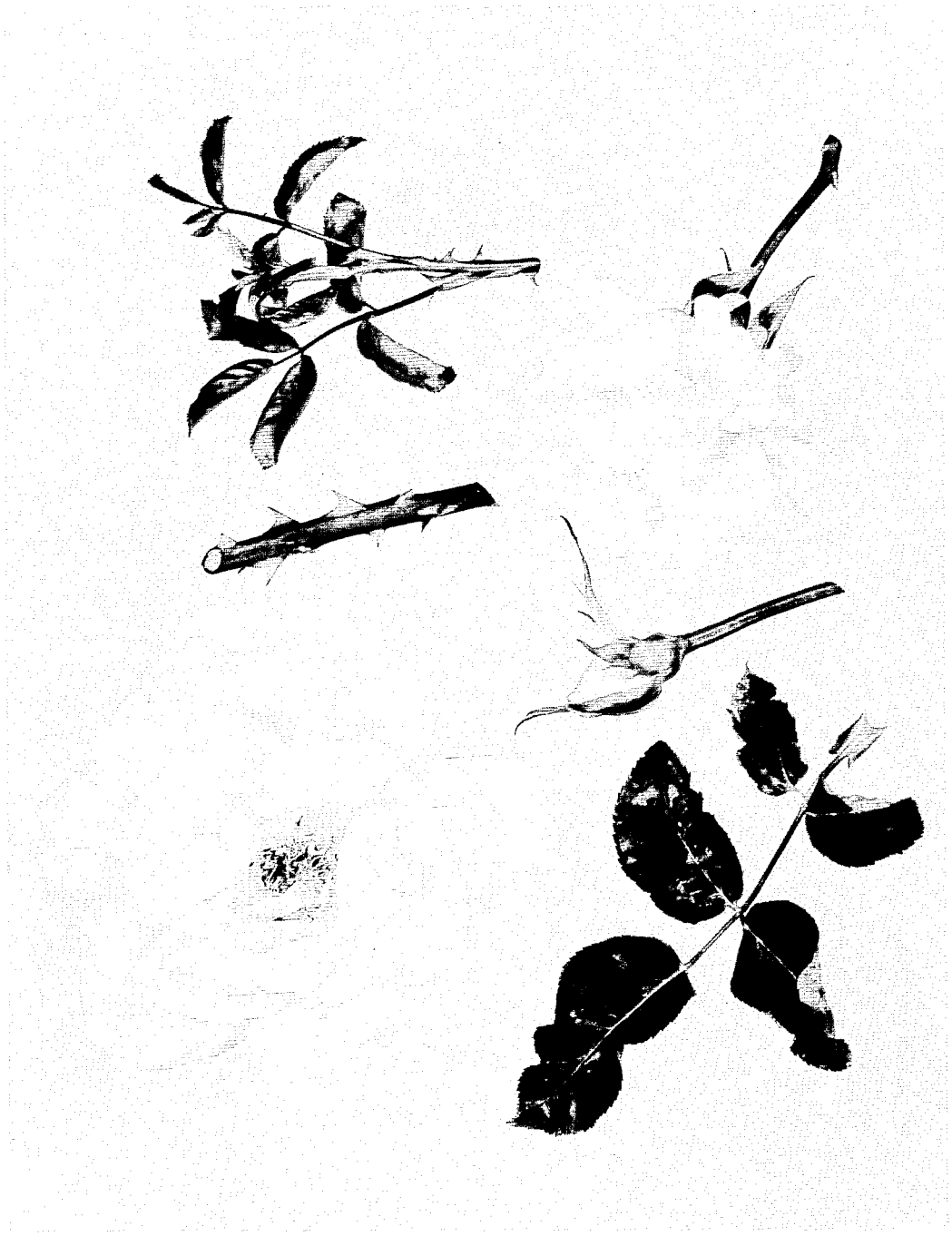
Inventor.
Wm. A. Warriner
By: Robb & Robb
Attorneys.

United States Patent Office

Plant Pat. 2,997
Patented Nov. 10, 1970

2,997

ROSE PLANT

William A. Warriner, Newark, N.Y., assignor to Jackson & Perkins Company, Newark, N.Y., a corporation of New York

Filed Dec. 9, 1968, Ser. No. 782,493
Int. Cl. A01h *5/00*
U.S. Cl. Plt.—15 1 Claim

The present invention relates to a new and distinct variety of rose plant of the hybrid tea class, which was originated by me by crossing the rose variety known as "South Seas" (Plant Pat. No. 2,184) with the rose variety known as "King's Ransom" (Plant Pat. No. 2,103), the former being the seed parent and the latter being the pollen parent.

The primary object of this breeding was to produce a new and improved rose variety of the hybrid tea class which bears large flowers in the yellow-orange color range on a vigorous and upright plant. This objective was fully achieved, along with other desirable improvements, as evidenced by the following unique combination of characteristics which are outstanding in the new variety and which distinguishes it from its parents, as well as from all other rose varieties of which I am aware:

(1) A vigorous and upright habit of growth;
(2) Long, strong and upright flower stems;
(3) Exceptionally large flowers; and
(4) A distinctive and attractive pale orange-yellow color effect of the flowers.

Asexual reproduction of my new variety of budding, as performed at both Livermore and Wasco, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature except where general color terms of ordinary dictionary significance are obvious:

Parentage: Seedling.
*Seed parent.*—"South Seas."
*Pollen parent.*—"King's Ransom."
Classification:
*Botanic.*—Rosa.
*Commercial.*—Hybrid tea.

FLOWER (Observations made from specimens grown in a greenhouse at Newark, N.Y., in the morning during the early part of the month of November.)

Blooming habit:
*Recurrent.*—Continuous.
Bud:
*Size.*—Very large.
*Form.*—Very long pointed.
*Color.*—When sepals first divide: Pinkish Cinnamon, Plate 2, 15″–b. When half-blown: Inside of petals—Capucine Buff, Plate 3, 13–f on upper half, blended into Chrome Yellow, Plate 4, 20–a on lower half. Reverse of petals—Light, Ochraceous-Salmon, Plate 15, 131–d, blended into Light Cadmium, Plate 4, 19 at lower quarter of petal.
*Sepals.*—Color: Inside—Biscay Green, Plate 17, 27′–i with whitish tomentum. Outside=Biscay Green, Plate 17, 27′–i overcast with Light Elm Green, Plate 17, 27′–k. Edge: Smooth.

*Receptacle.*—Color: Biscay Green, Plate 17, 27′–i. Shape: Apple, Size: Large; broad. Surface: Smooth.
*Peduncle.*—Length: Very long. Surface: Smooth. Color: Light Elm Green, Plate 17, 27′–k.
Bloom:
*Size.*—Very large.
*Borne.*—Singly.
*Stems.*—Long.
*Form (when first open).*—High-centered. Permanence: Flattens.
*Petalage.*—Number of petals under normal conditions: From 20 to 25.
*Color.*—Inside of petals: Pale Orange-Yellow, Plate 3, 17–f. Reverse of petals: Capucine Buff, Plate 3, 13–f. Base of petals: Chrome Yellow, Plate 4, 20–a. General tonality from a distance: Pale orange-yellow. Discoloration: Becomes Seashell pink, Plate 14, 11′–f about third day.
*Fragrance.*—Fruity.
Petals:
*Texture.*—Leathery.
*Surface.*—Inside: Satiny. Reverse: Smooth.
*Form.*—Round.
*Arrangement.*—Imbricated.
*Persistence.*—Drop off cleanly.
*Lasting quality.*—On the plant: Long. As cut flower: Long.

REPRODUCTIVE ORGANS

Anthers: Large; regularly arranged around styles.
*Color.*—Yellow.
Filaments (threads): Some long and some medium length.
*Color.*—Yellow.
Pollen:
*Color.*—Lemon yellow.
Fruit:
*Form.*—Round.
*Color (at maturity).*—Greenish yellow.
*Sepals.*—Curled.

PLANT

Form: Bush.
Growth: Very vigorous.
Foliage:
*Leaves.*—Compound of 5 leaflets.
*Leaflets.*—Size: Large. Quantity: Normal. Color: New foliage—Upper side —Bronzy. Old foliage: Upper side—Empire Green, Plate 32, 33″–m. Under side—Spinach Green, Plate 5, 29–m. Shape: Elliptical. Texture: Upper side—Leathery. Under side—Rough. Ribs and veins: Ordinary. Edge: Serrated. Single. Petiole (rachis): Color—Spinach Green, Plate 5, 29–m. Under side—Few prickles. Stipules: Short; smooth.
*Disease resistance.*—Mildly susceptible to mildew and blackspot, as determined by comparison with other rose varieties grown under the same conditions at Newark, N.Y.
Wood:
*New Wood.*—Color: Light Green. Bark: Smooth.
Thorns:
*Quantity.*—Few on main stalks.
*Form.*—Long, narrow base; slightly hooked downward.
*Color.*—Old: Amber Brown, Plate 3, 13–k. When young: Courge Green, Plate 17, 25′–i.
*Position.*—Irregular.
Prickles: Few on both main stalks and on laterals.

I claim:

1. A new and distinct variety of rose plant of the hybrid tea class, substantially as herein shown and described, characterized particularly as to novelty by the unique combination of a vigorous and upright habit of growth, long, strong and upright flower stems, exceptionally large flowers, and a distinctive and attractive pale orange-yellow color effect of the flowers.

No references cited.

ROBERT E. BAGWILL, Primary Examiner